US00PP32147P2

(12) United States Plant Patent
Rat

(10) Patent No.: US PP32,147 P2
(45) Date of Patent: Sep. 1, 2020

(54) PEONY PLANT NAMED 'RTPIV 789-03'

(50) Latin Name: ***Paeonia lactiflora* x *Paeonia lutea* hybrid**
Varietal Denomination: RTPIV 789-03

(71) Applicant: Early Morning LLC, Greendale, IN (US)

(72) Inventor: Thierry Rat, Moissac (FR)

(73) Assignee: Early Morning LLC, Greendale, IN (US)

( * ) Notice: Subject to any disclaimer, the term of this patent is extended or adjusted under 35 U.S.C. 154(b) by 0 days.

(21) Appl. No.: 16/602,832

(22) Filed: Dec. 9, 2019

(51) Int. Cl.
*A01H 5/02* (2018.01)

(52) U.S. Cl.
USPC ..... Plt./316

(58) Field of Classification Search
USPC ..... Plt./316
See application file for complete search history.

*Primary Examiner* — Annette H Para
(74) *Attorney, Agent, or Firm* — Barbara Campbell; Cochran Freund & Young LLC

(57) ABSTRACT

A new and distinct variety of peony plant having red-purple flowers, a perennial herbaceous shrub, having a compact, symmetrically rounded, and vigorous growth habit, is disclosed.

1 Drawing Sheet

Genus and species: *Paeonia lactiflora* x *Paeonia lutea* hybrid.

Denomination: 'RTPIV 789-03'.

BACKGROUND

'RTPIV 789-03' is a new and distinct variety of *Paeonia lactiflora* x *Paeonia lutea* hybrid. 'RTPIV 789-03' originated from a controlled cross in May 2007 in France between the female parent 'Miss America' (unpatented) and the male parent 'Chinese Dragon' (unpatented).

The resulting seeds from the cross were collected and planted and evaluated in France. 'RTPIV 789-03' was selected in May 2013 from the population of seedlings in France. 'RTPIV 789-03' was first asexually propagated in October 2015 in France from vegetative cuttings.

'RTPIV 789-03' reproduces true to type in successive generations of asexual reproduction via vegetative cuttings.

SUMMARY

The following are the most outstanding and distinguishing characteristics of this new variety when grown under normal horticultural practices in France.

1. Red-purple flowers; and
2. A perennial herbaceous shrub, having a compact, symmetrically rounded, and vigorous growth habit.

DESCRIPTION OF THE PHOTOGRAPHS

This new peony plant is illustrated by the accompanying photographs which show the plant's overall plant habit including form, foliage, and flowers. The photographs are of a six to eight years-old plant grown outdoors in France in May 2019. The colors shown are as true as can be reasonably obtained by conventional photographic procedures.

DETAILED DESCRIPTION

Figure 1:
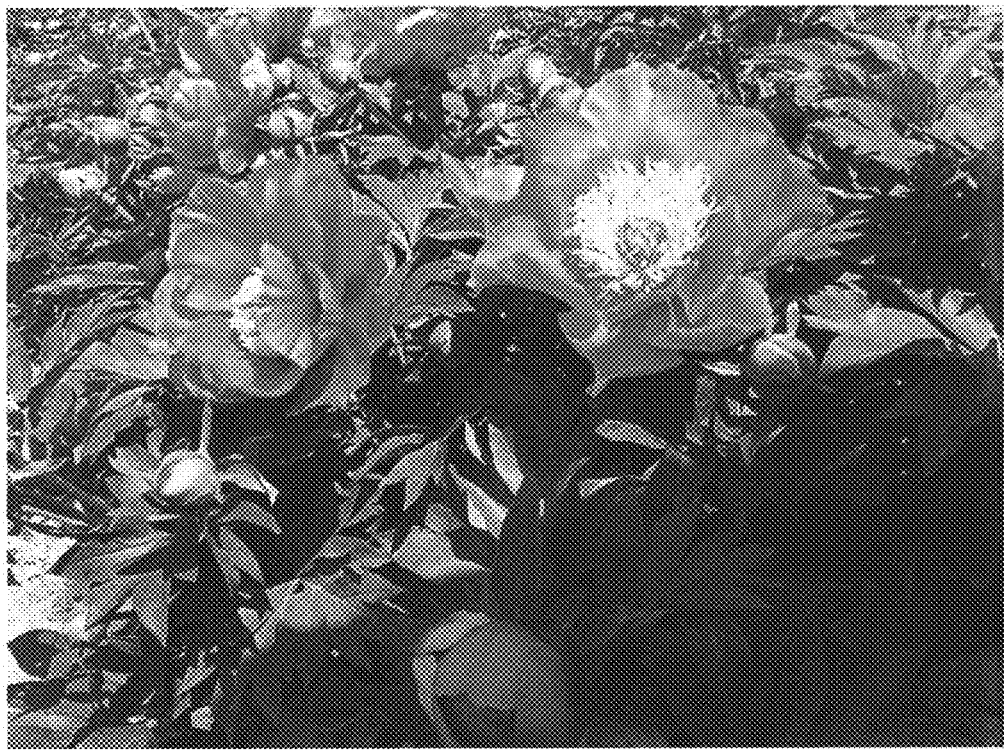
FIG. 1 shows the overall plant habit and buds, flowers, and foliage of 'RTPIV 789-03'.
Figure 2:
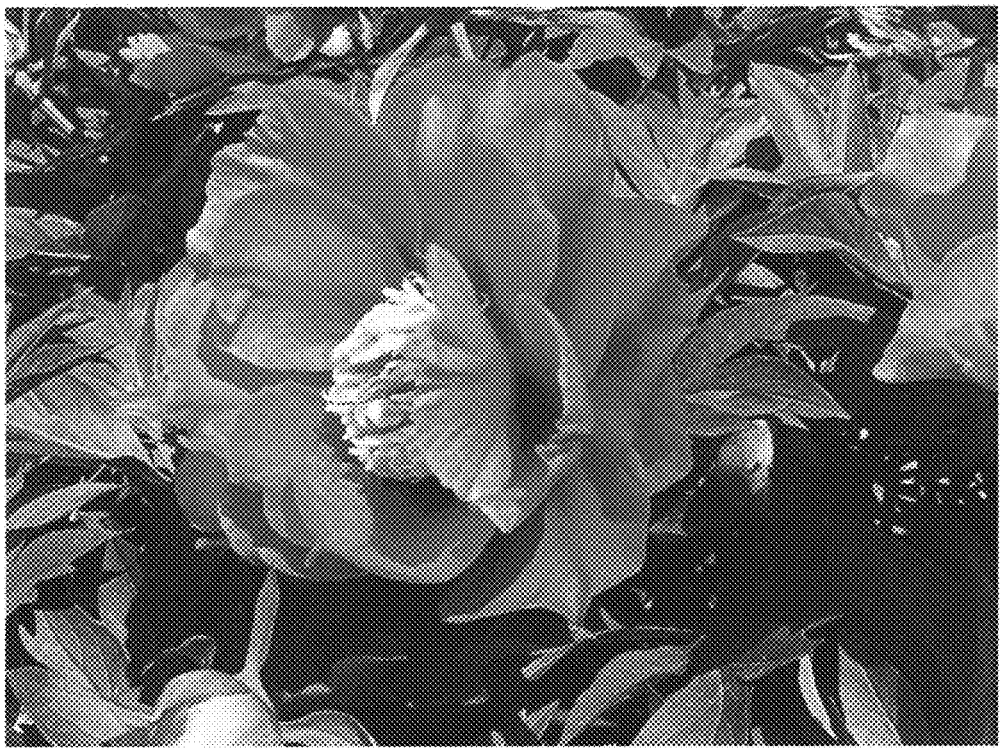
FIG. 2 shows a close-up of an individual open flower.

The following detailed descriptions set for the distinctive characteristics of 'RTPIV 789-03'. The data which define these characteristics were collected outdoors in France in 2017. The plants were six to eight years-old when the descriptions were taken. Color references are to The R.H.S. Colour Chart of The Royal Horticultural Society of London (R.H.S.) 2001, except where general terms of ordinary dictionary significance are used.

Classification:
- *Family*.—Paeoniaceae.
- *Species*.—*Paeonia lactiflora* x *Paeonia lutea* hybrid.
- *Variety*.—'RTPIV 789-03'.

Parentage:
- *Female parent*.—'Miss America' (unpatented).
- *Male parent*.—'Chinese Dragon' (unpatented).

Plant:
- *Type*.—Vegetative cuttings.
- *Root description*.—Fleshy storage root.
- *Rooting habit*.—Freely branching storage and feeder roots.
- *Growth habit*.—Perennial herbaceous shrub; compact and symmetrically rounded; vigorous growth habit.
- *Plant height*.—70 cm to 80 cm.
- *Plant width*.—80 cm to 100 cm.

Stem:
- *Quantity of flowers per branch*.—3 to 5.
- *Length*.—70 cm to 80 cm.
- *Diameter between first and 2nd leaf*.—1.05 cm.
- *Internode length (highly variable)*.—5 cm to 6 cm.
- *Aspect*.—Mostly upright.
- *Strength*.—Strong.
- *Color*.—RHS 144C (Yellow-Green).

Leaf:

*Arrangement*.—Alternate, biternately compound with three primary leaflets further divided into second leaflets of variable number and form.

*Leaf length* (*including petiole*).—30 cm to 35 cm.

*Leaf width*.—25 cm to 30 cm.

*Leaflet length* (*central*).—15 cm to 16 cm.

*Leaflet width* (*central*).—12 cm to 13 cm.

*Leaflet shape*.—Broadly elliptical, variably incised.

*Leaflet apex*.—Broadly acuminate, often with emargination.

*Leaflet base*.—Attenuate.

*Leaflet margin*.—Deeply incised with light purple edge.

*Leaflet texture* (*both upper and lower surfaces*).—Smooth, glabrous.

*Leaflet venation pattern*.—Pinnate; reticulate.

*Leaf color*.—Upper surface: RHS 147B (Yellow-Green). Lower surface: RHS 191B (Yellow-Green).

*Venation* (*lower surface*).—RHS 145D (Yellow-Green).

*Petiole*.—Length (of the 2nd leaf): 11 cm. Diameter: 0.6 cm. Color: RHS 145D (Yellow-Green).

Flower: Flower shape, arrangement and flowering habit; single flower/peduncle; flower terminal or axillary; flower face upright to outward; flower arranged above foliage.

*Natural flower season* (*south-west of France*).—Plants begin flowering about 60 days after bud break in early spring.

*Flower longevity*.—Flower last about 8 to 12 days on the plant.

*Fragrance*.—Mild.

*Flower buds*.—Length: 4 cm. Diameter: 3.5 cm. Shape: Globose. Color: RHS 144A (Yellow-Green).

*Flowers*.—Diameter: 15 cm to 16 cm. Depth: 7 cm to 8 cm. Petals: Quantity (main flower): 12 to 15. Length: 8 cm to 9 cm. Width: 7 cm. Shape: Rounded. Apex: Frequently emarginate. Margin: Entire to sinuate. Texture, upper and lower surfaces: Smooth, glabrous. Color: RHS 67A (Red-Purple). Flare: RHS 66A (Red-Purple). Sepals: Quantity: 2 small and 3 large. Length: 4.0 cm. Width (outer): 4.0 cm. Shape: Obcordate to obovate; cupped. Apex: Mucronate. Margin: Entire to slightly sinuate. Color: RHS 144B (Yellow-Green) at the base, RHS 183C (Greyed-Purple) on remaining surface. Peduncles (main bud): Length : 12 cm to 15 cm. Diameter: 0.6 cm. Strength: Strong. Texture: Smooth, with few hairs. Color: RHS 144C (Yellow-Green).

Reproductive organs:

*Stamen*.—Quantity per flower: About 80. Filament length: 2.5 cm. Filament color: RHS 63C (Red-Purple). Anther shape: Lightly elongated and curved. Anther Length: 1 cm. Anther color: RHS 6D (Yellow). Pollen amount: Moderate.

*Pistil*.—Quantity per flower: 4 to 5. Length: 3 cm. Stigma shape: Claw-shaped, convex. Stigma color: RHS 62A (Red-Purple). Ovary color: RHS 142D (Green-Yellow).

*Floral disk*.—Strength: Strong. Color: RHS 142D (Green-Yellow).

Fruit and seed set: Seed production has not been observed.

Disease and insect resistance: Excellent resistance; but no particular susceptibility to diseases or pests.

Temperature tolerance: Hardy like other intersectional hybrid peonies.

COMPARISON WITH PARENTAL AND COMMERCIAL LINES

Table 1 shows a comparison of differences between 'RTPIV 789-03' and both parental lines.

TABLE 1

Comparison with Parental Lines

| Characteristic | 'RTPIV 789-03' | Female parent, 'Miss America' | Male parent, 'Chinese Dragon' |
|---|---|---|---|
| Flower color | Red-Purple | White | Blood red to deep cerise |

Table 2 shows a comparison of the differences between 'RTPIV 789-03' and the commercial peony variety 'Coral Charm' (U.S. Plant Pat. No. 4,247).

TABLE 2

Comparison with Commercial Line

| Characteristic | 'RTPIV 789-03' | 'Coral Charm' |
|---|---|---|
| Flower color | Red-Purple | Orange-coral |

I claim:

1. A new and distinct variety of peony plant designated 'RTPIV 789-03' as illustrated and described herein.

* * * * *